United States Patent
Bzoch

[19]

[11] Patent Number: 6,039,709
[45] Date of Patent: Mar. 21, 2000

[54] ORTHOPEDIC HINGE ASSEMBLY

[75] Inventor: Jan J. Bzoch, Treasure Island, Fla.

[73] Assignee: Orthosis Corrective Systems, Pirellas Park, Fla.

[21] Appl. No.: 09/212,224

[22] Filed: Dec. 16, 1998

[51] Int. Cl.[7] .................................................. A61F 5/00
[52] U.S. Cl. .............................................. 602/26; 602/16
[58] Field of Search .................................. 602/5, 16, 19, 602/20, 21, 22, 23, 24, 26, 27–30; 623/18, 19, 20, 27, 28, 39, 45, 47, 48, 58, 59–63; 482/114, 115; 606/57, 58, 70, 71, 54, 55; 601/33, 34; 16/277, 284, 292, 343, 325, 327, 341

[56] References Cited

U.S. PATENT DOCUMENTS

| | | | |
|---|---|---|---|
| 4,881,229 | 11/1989 | Young et al. | 16/371 |
| 5,000,170 | 3/1991 | Young et al. | 623/39 X |
| 5,460,599 | 10/1995 | Davis et al. | 602/16 |
| 5,507,719 | 4/1996 | Freeman | 602/26 |
| 5,662,595 | 9/1997 | Chesher et al. | 602/20 |

*Primary Examiner*—Kim M. Lee
*Attorney, Agent, or Firm*—Larson & Larson, P.A.; James E. Larson

[57] ABSTRACT

The assembly has a pair of opposed exterior plates containing slots for receiving an adjustment wheel threaded to a screw positioned in close association with gear teeth juxtaposed to the second end portion of a first elongated bar. The exterior plates enclose the second end of two elongated bars. The first end of each bar is positioned within oppositely positioned pockets in an orthopedic device. Gear teeth integral with the second end portion of the second elongated bar engage the gear teeth on a cam gear juxtaposed to the second end portion of the first elongated bar. The exterior plates are locked together with rivets to hold the gear teeth in position and permit movement or locking of the second elongated bar by manipulation of the adjustment wheel.

16 Claims, 7 Drawing Sheets

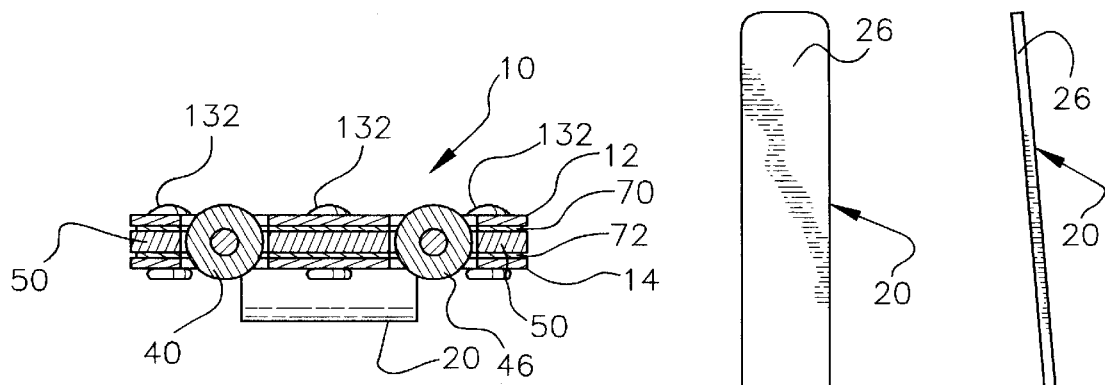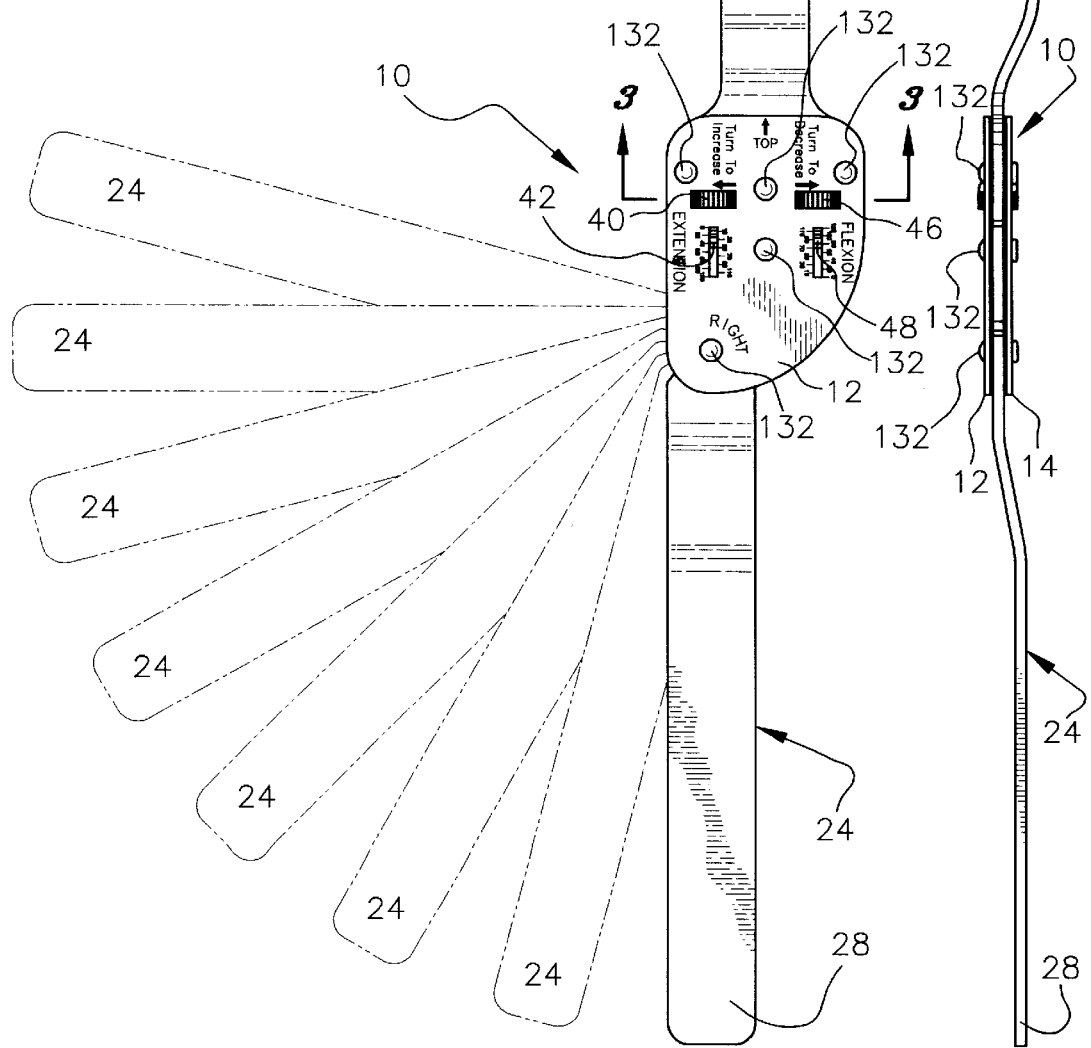

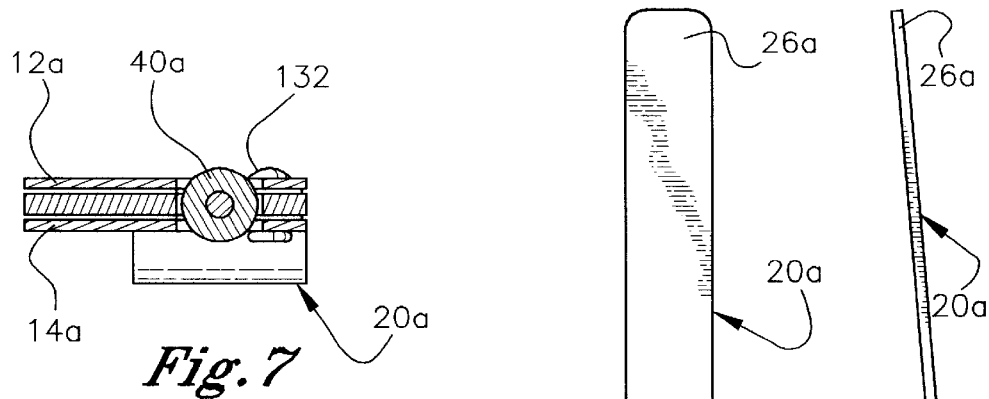
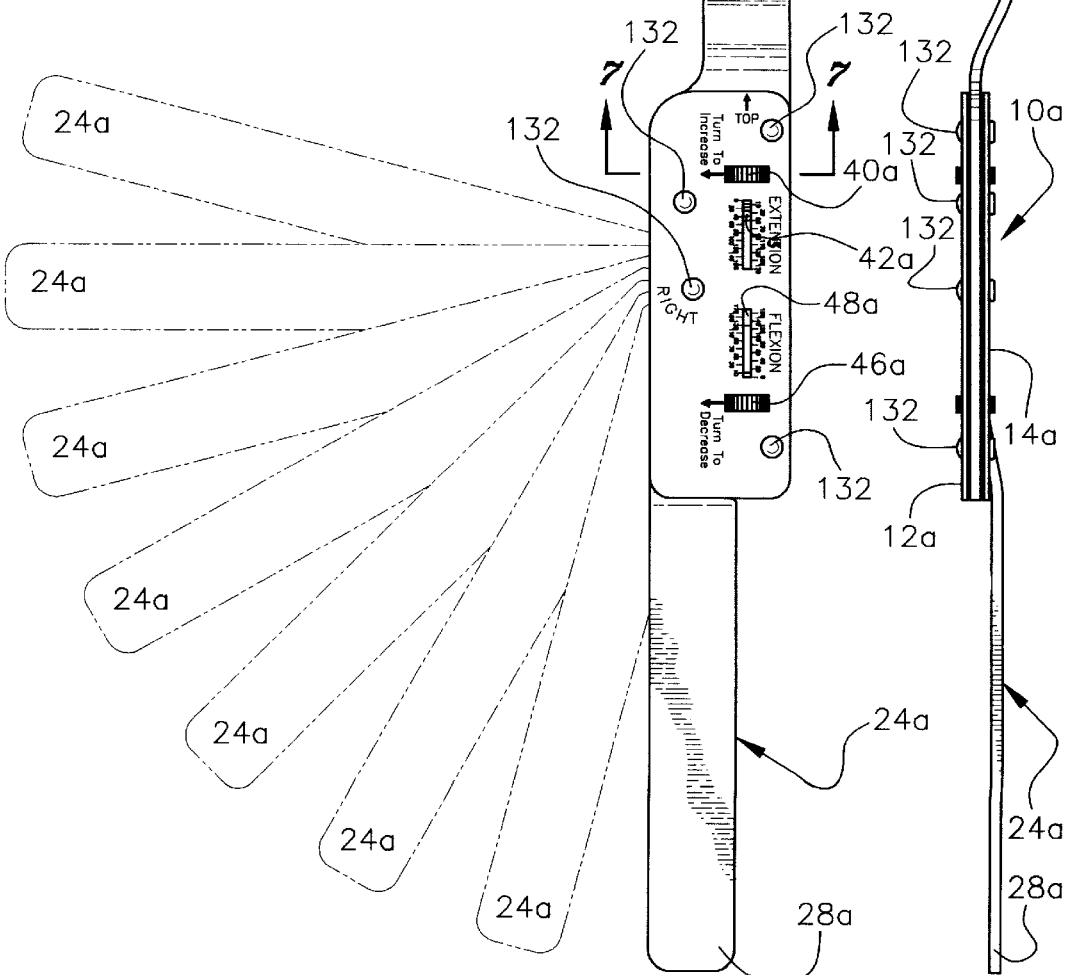
Fig.7
Fig.5
Fig.6

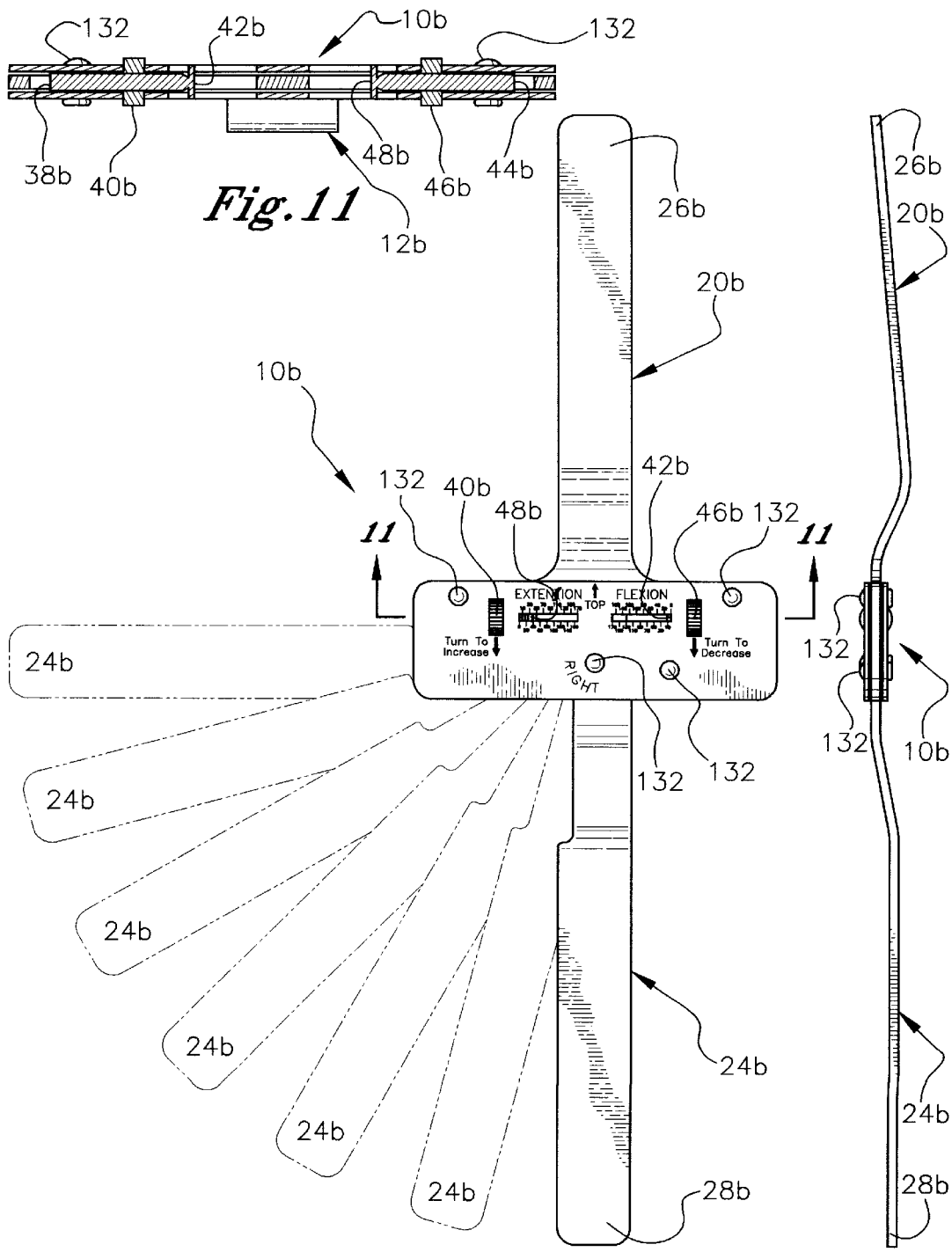

ORTHOPEDIC HINGE ASSEMBLY

BACKGROUND OF THE INVENTION

The invention relates to a hinge assembly for use with orthopedic devices. More particularly, it refers to an articulated orthopedic hinge that can be set for maximum movement of a patient's limb.

Hinge assemblies such as shown in U.S. Pat. 5,460,599 are well known for use in positioning orthopedic devices. The most common use for such hinge assemblies is with an orthopedic knee brace. A hinge assembly is positioned on each side of the knee joint of the patient to control the amount of flexion and extension of knee movement. The hinge assembly is adjustable and contains a device for locking the angle or range of movement without needing additional tools.

Although many of the prior art adjustable and locking hinge assemblies serve their intended purpose, difficulty in ease of setting the desired degrees of flexion and extension continues to be a problem.

SUMMARY OF THE INVENTION

The present invention provides an easily adjustable and firmly lockable improved orthopedic hinge assembly. The assembly has a pair of opposed exterior plates containing slots for receiving flexion and extension adjustment wheels each threaded to a screw. The exterior plates enclose a second end of each of two elongated bars. The first end of each elongated bar fits into oppositely positioned pockets in an orthopedic device. Gear teeth mounted on a cam juxtaposed to the second end portion of the first elongated bar engage with gear teeth integral with the second end portion of the second elongated bar. The rotating motion of each wheel adjusts the threaded screw with respect to the gear teeth. The exterior plates are locked together with rivets to hold the gear teeth in position and permit movement or locking of the second elongated bar by manipulation of the adjustment wheels.

BRIEF DESCRIPTION OF THE DRAWINGS

The invention may be best understood by those having ordinary skill in the art by reference to the following detailed description when considered in conjunction with the accompanying drawings in which:

FIG. 1 is a top plan view of the hinge assembly of this invention showing the different positions of the second elongated bar in phantom.

FIG. 2 is a side elevational view of the hinge assembly.

FIG. 3 is a cross sectional view of the hinge assembly along lines 3—3 of FIG. 1.

FIG. 5 is a top plan view of a first alternate hinge assembly.

FIG. 6 is a side elevational view of the first alternate hinge assembly.

FIG. 7 is a cross sectional view of the first alternate hinge assembly along lines 7—7 of FIG. 5.

FIG. 9 is a top plan view of a second alternate hinge assembly.

FIG. 10 is a side elevational view of the second alternate hinge assembly.

FIG. 11 is a cross sectional view of the second alternate hinge assembly along lines 11—11 of FIG. 9.

DETAILED DESCRIPTION OF THE INVENTION

Figure 4:
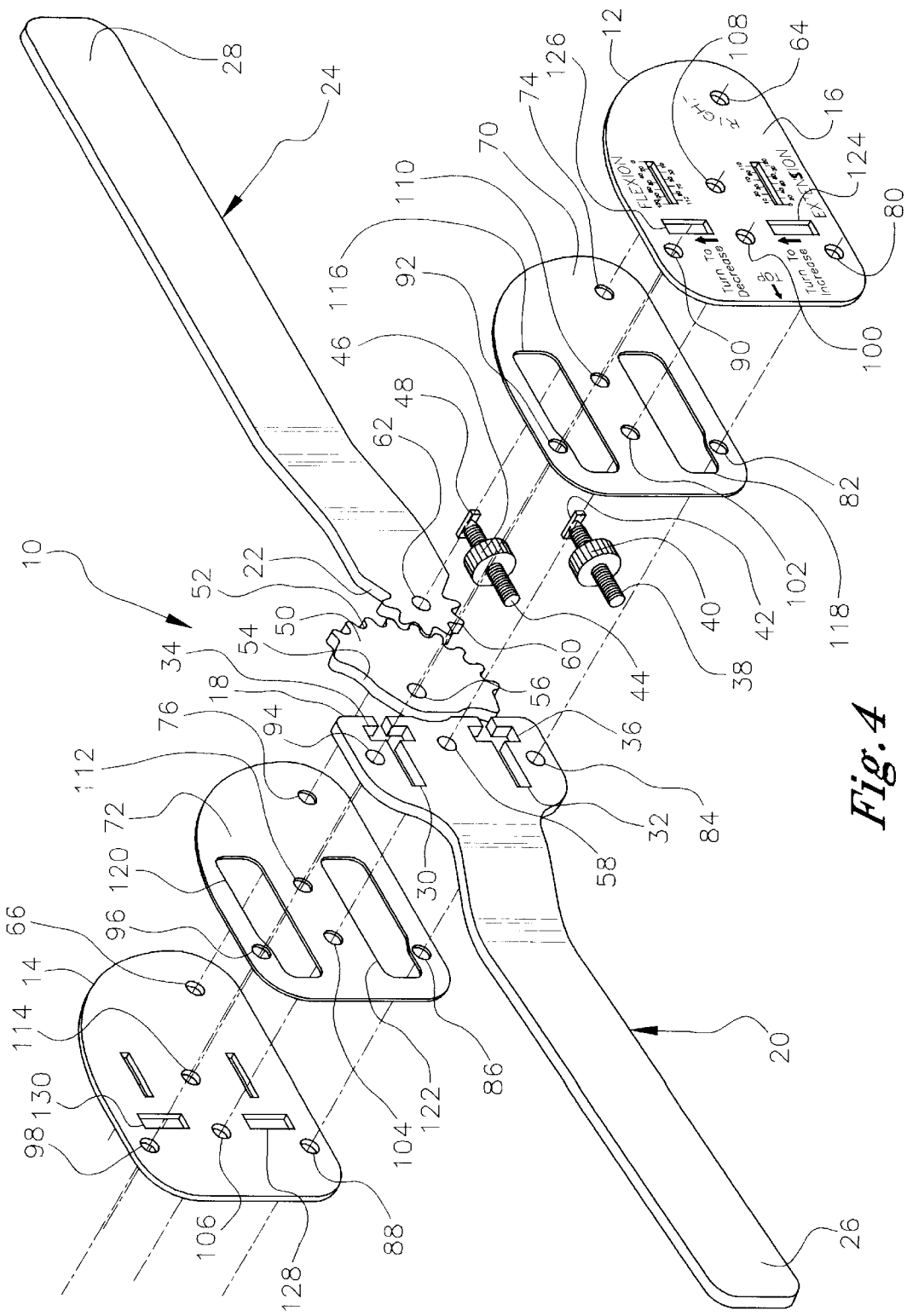
FIG. 4 is an exploded view of the hinge assembly.
Figure 8:
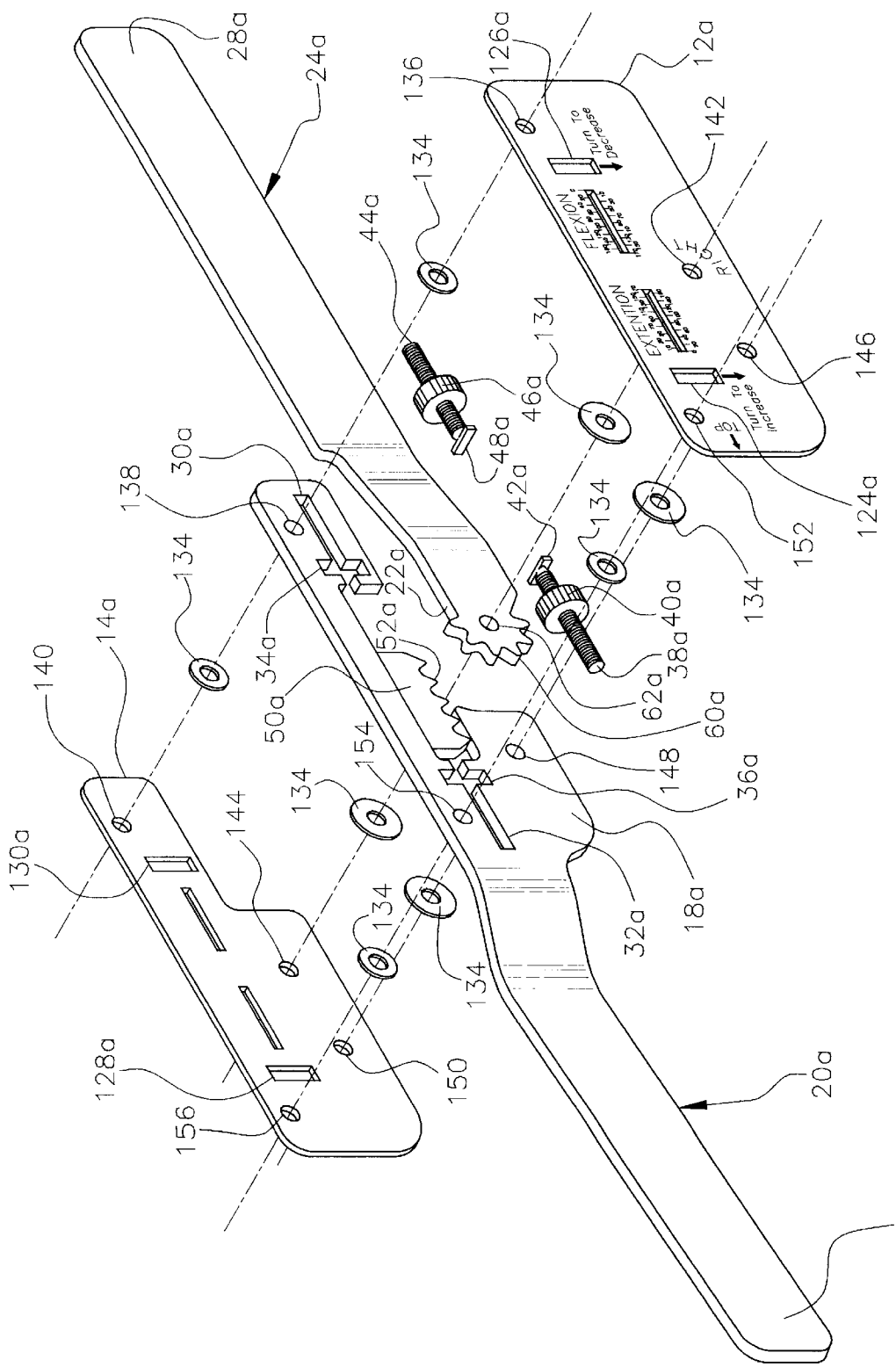
FIG. 8 is an exploded view of the first alternate hinge assembly.
Figure 12:
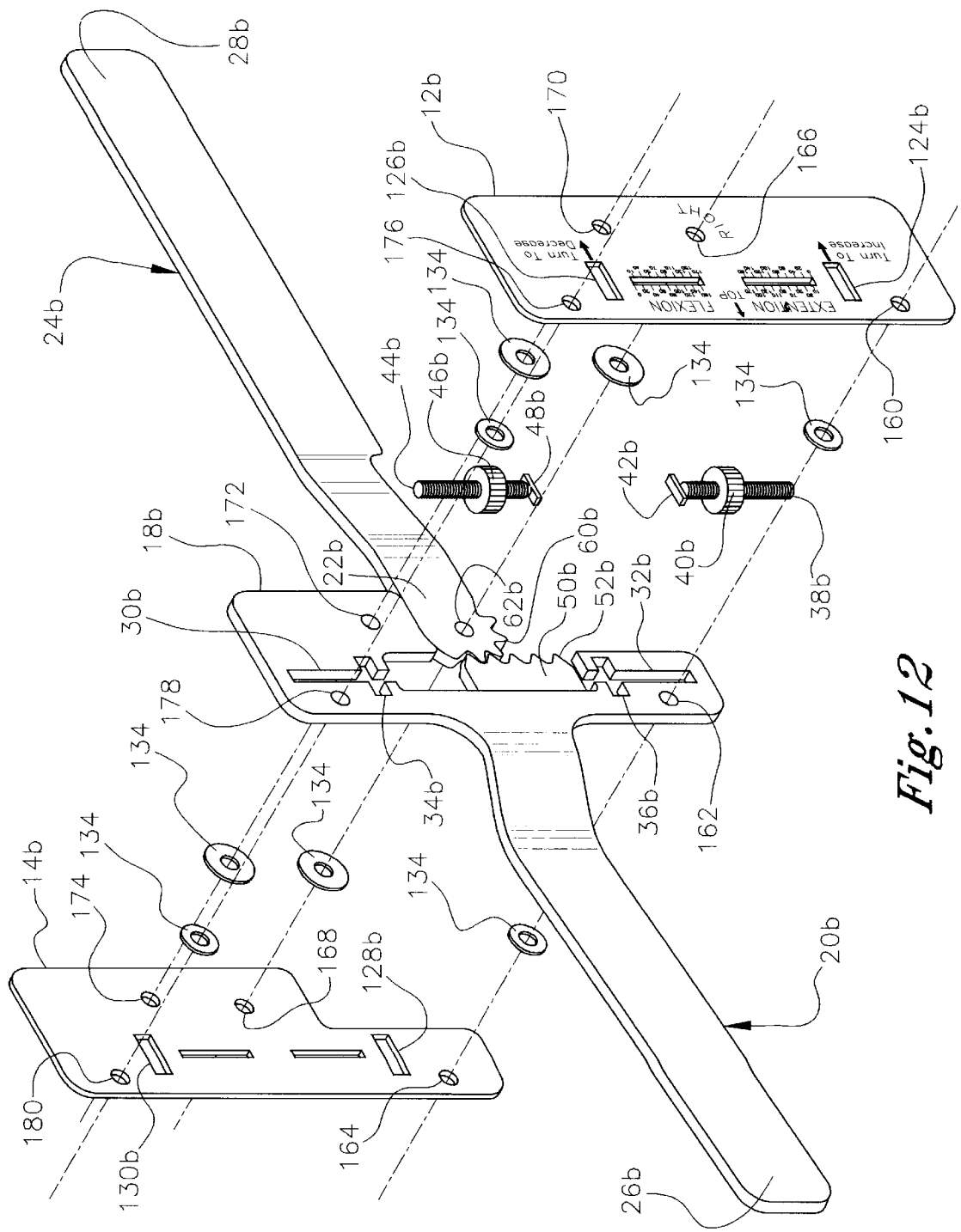
FIG. 12 is an exploded view of the second alternate hinge assembly.

Throughout the following detailed description, the same reference numerals refer to the same elements in all figures.

Referring to FIGS. 1–4, the hinge assembly of this invention 10 has a top plate 12 and a bottom plate 14. The top surface 16 of plate 12 contains indicia to instruct a user how to set the hinge assembly 10. The plates 12 and 14 enclose the second end portion 18 of a first elongated bar 20 and the second end portion 22 of a second elongated bar 24.

Figure 13:
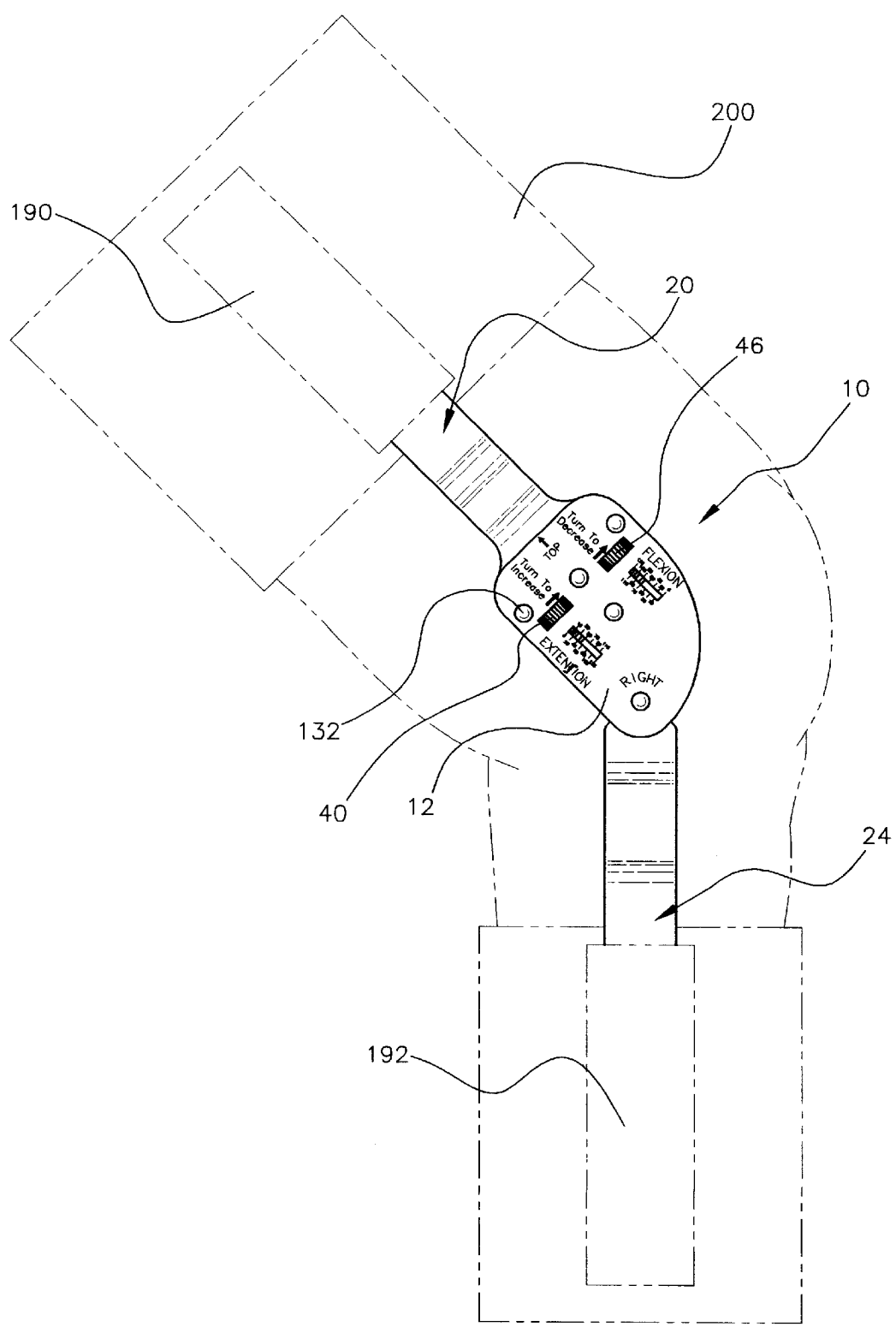
FIG. 13 is an isometric view of one hinge assembly of this invention mounted on the right side of a patient's knee in pockets of a fabric splint shown in phantom.

A first portion 26 of a first elongated bar 20 and a first portion 28 of the second elongated bar 24 fit into oppositely positioned pockets 190 and 192 respectively on an orthopedic device 200 as shown in FIG. 13. Alternatively, the portions 26 and 28 of bars 20 and 24, respectively can be held in place by hook and loop straps attached to an orthopedic device.

The second end portion 18 of elongated bar 20 has horizontal slots 30 and 32, respectively. These horizontal slots 30 and 32 are joined to vertical slots 34 and 36, respectively. A first threaded screw 38 fits into slot 32 and a wheel 40 threaded to screw 38 fits into vertical slot 36. A stop 42 at one end of screw 38 is used to engage a cam gear 50 which will be discussed hereafter. A second screw 44 having a threaded wheel 46 and a stop 48 are positioned respectively in slots 30 and 34.

The cam gear 50 is juxtaposed to the second end portion 18 of elongated bar 20. The cam gear 50 has gear teeth 52 on one side and a cam surface 54 on another side. A hole 56 is aligned with holes 108 in top plate 12 and hole 114 in bottom plate 14. The second end portion 22 of the second elongated bar 24 has integral gear teeth 60 in a circular pattern meshing with gear teeth 52 on the cam gear 50 to move bar 24. A hole 62 in the second end portion 22 of the elongated bar 24 is aligned with holes 64 in plate 12 and hole 66 in plate 14. An interior plate 70 is interposed between plate 12 and the cam gear 50 and the second end portions 18 and 22 of both elongated bars 20 and 24, respectively. Another interior plate 72 is interposed between end portions 18 and 22 of the elongated bar 20 and elongated bar 24, respectively and an interior surface of plate 14. Holes 74 on plate 70 and holes 76 on plate 72 are aligned with holes 64 and 66 on exterior plates 12 and 14, respectively.

Hole 80 on plate 12, hole 82 on plate 70, hole 84 on the second portion 18 of elongated bar 20, hole 86 on plate 72 and hole 88 on plate 14 are all in alignment and receive a rivet 132 in order to hold the hinge assembly 10 in position. In addition, hole 90 in plate 12, hole 92 in plate 70, hole 94 in the second portion of the elongated bar 20, hole 96 in plate 72 and hole 98 in plate 14 are all in alignment and also receive a rivet 132 to hold the hinge assembly 10 in place. Hole 100 in exterior plate 12, hole 102 in interior plate 70, hole 58 in second end 18 of elongated bar 20, hole 104 in interior plate 72 and hole 106 in exterior plate 14 are all in alignment and receive a rivet 132. Holes 108 on plate 12, hole 110 on plate 70, hole 56 in cam gear 50, hole 112 on plate 72 and hole 114 on plate 14 are in alignment and held in place with a rivet 132. The cam gear 50 pivots on the rivet.

Plate 70 has openings 116 and 118 and plate 72 has openings 120 and 122 to accommodate the wheels 40 and 46 attached to screws 38 and 44, respectively. Wheel 40 fits through slot 124 on plate 12 and wheel 46 fits through slot 126 on plate 12. In like manner, wheel 38 fits through slot 128 on plate 14 and wheel 46 fits through slot 130 on plate 14.

Elongated bar 24 pivots at hole 62 on its rivet 132.

Rivets 132 hold the hinge assembly 10 in position through the various aligned holes and permit pivoting at hole 56 and 62. Alternatively, a screw and bolt arrangement could be used in place of rivets.

Movement of wheel 40 within slots 124 and 128 causes lateral movement of screw 38 to affect extension of elongated bar 24 by causing stop element 42 to contact cam gear 50 which in turn, causes movement of elongated bar 24. Turning of wheel 46 within slots 126 and 130 causes lateral movement of screw 44 and its terminal stop element 48 pressing against cam gear 50 affects the flexion controlled by elongated bar 24.

Turning to FIGS. 5–8, a first alternative hinge assembly is set forth. Exterior plates 12a and 14a enclose a first elongated bar 20a and a second elongated bar 24a. First end portion 26a of elongated bar 20a and portion 28a of elongated bar 24a are inserted into a pocket of an orthopedic device as shown in FIG. 13. A second end portion 18a of elongated bar 20a is juxtaposed to a moveable cam gear 50a with gear teeth 52a. Elongated bar 20a has at its second end portion 18a a slot 32a to accommodate a screw 38a and a slot 36a at right angles to slot 38a to accommodate wheel 40a riding on the threaded screw 38a. A stop element 42a is at one end of the screw 38a and engages the cam gear 50a in order to control extension of the orthopedic device 10a. The second elongated bar 24a has at a second end 22a a circular pattern of gear teeth 60a engaging the gear teeth 52a on the cam gear 50a. A slot 30a on an extension of end portion 18a accommodates threaded screw 44a and slot 34a accommodates the wheel 46a threaded to the screw 44a. A terminal end 48a of the screw 44a engages cam gear 50a in order to control flexion. A hole 126a on plate 12a and 130a on plate 14a accommodates the wheel 46a. Hole 124a on plate 12a and 128a on plate 14a accommodates wheel 40a. Holes on the various components accommodate rivets 132. Holes 142, 62a and 144 are aligned to receive a rivet 132. The second elongated bar 24a pivots around the rivet in hole 62a. Holes 146, 148 and 150 are aligned to receive a rivet 132. Holes 152, 154 and 156 are aligned to receive a rivet 132. Holes 136, 138 and 140 are aligned in order to receive a rivet 132. Washers 134 are inserted between plate 12a and the second end of the elongated bars 20a and 24a in alignment with the holes. Washers are installed between the plate 14a and the second end portion of elongated bars 20a and 24a in alignment with the holes. The washers 134 accommodate sealing of the exterior of plates 12a and 14a around the elongated bars 20a and 24a.

The second alternative design is set forth in FIGS. 9–12, in which plates 12b and 14b surround the second end 18b and 22b of elongated bars 20b and 24b, respectively. Slot 124b on plate 12b and 128a on plate 14b accommodate wheel 40b secured to threaded screw 38b. Screw 38b has an end element 42b for engaging cam gear 50b. In like manner, slot 126b of plate 12b and slot 130b of plate 14b accommodate wheel 46b threaded to screw 44b and having a terminal end 48b. Slot 32b on the end portion 18b of elongated bar 20b accommodates the screw 38b and slot 36b accommodates the wheel 40b in order to control extension of the elongated bar 24b. In order to control flexion, wheel 46b is located in slot 34b of the second end of the elongated bar 20b and the wheel 46b rides on a threaded screw 44b which fits into slot 30b. The extension member 48b on the screw 44b engages the cam gear 50b which has gear teeth 52b engaging gear teeth 60b at the end of elongated bar 24b.

Rivets 132 hold the plates 12b and 14b around the portions 18b and 22b of the elongated members 22b and 24b, respectively. One rivet 132 is fitted in alignment through holes 160, 162 and 164. A second rivet is inserted through holes 166, 62b and 168. The elongated bar 24b pivots on the rivet going through hole 62b. A third rivet fits through holes 170, 172 and 174 and a fourth rivet fits through holes 176, 178 and 180. Washers 134 are inserted between plate 12b and the second end of the elongated bar 20b and 24b in alignment with the holes. Washers are installed between plate 14b and the second end portion of elongated bars 20b and 24b in alignment with the holes. The washers 134 accommodate sealing of the exterior plates 12b and 14b around the elongated bars 20b and 24b.

A hinge assembly 10 is usually mounted on each side of a knee with one elongated bar 20 inserted in pocket 190 of a knee brace 200. The other elongated bar 24 is inserted in pocket 192, all as shown in FIG. 13. The wheel 40 is set at the same position on each hinge assembly 10 to provide the desired extension of the brace. The wheel 46 is set at the same position on each hinge assembly 10 to provide the desired flexion of the brace.

The hinge assembly 10 as described is fully adjustable to a degree of contracture with complete control of either flexion or extension. No additional tools are needed. The assembly 10 can be easily adjusted by turning the wheels 40 or 46 as range of motion increases to accommodate a restorative therapy program. The wide range of flexion and extension settings offers patient comfort while increasing range of motion of the lower extremity.

The hinge assembly of this invention is made of a stainless steel or heavy duty aluminum. It also can be made of a high strength polymer.

Equivalent items can be substituted for the various elements of the present invention in order to carry out the invention in the same way and with the same function.

I claim:

1. An orthopedic hinge assembly for connecting portions of an orthopedic device, comprising:

(a) a pair of opposed exterior plates containing indicia on an exterior surface of at least one exterior plate and at least a first and second spaced apart slot on each opposed exterior plate in which a threaded thumb wheel mounted on a threaded adjustment screw is received;

(b) a first elongated bar having a first end portion insertable into a first pocket on the orthopedic device and having a second end portion containing a first and second spaced apart slot, each slot receiving the threaded adjustment screw and thumb wheel and aligned respectively with the first and second spaced apart slots on the exterior plates respectively;

(c) a second elongated bar having a first end portion insertable into a second pocket of the orthopedic device and having at a second end portion integral gear teeth;

(d) a cam gear juxtaposed to the second end portion of the first elongated bar engageable with the gear teeth at the second end portion of the second elongated bar;

(e) the second end portion of the first elongated bar and the second end portion of the second elongated bar together with the cam gear enclosed by the opposed exterior plates; and (f) means for joining the exterior plates together to retain the adjustment screws in position so that the thumb wheels can be turned to adjust the position of the second elongated bar with respect to the first elongated bar.

2. The orthopedic hinge assembly according to claim 1 wherein the means for joining the exterior plates together are multiple rivets passing through the exterior plates in aligned holes.

3. The orthopedic hinge assembly according to claim 2 wherein the second end portion of the second elongated bar has an axial hole accommodating one of the rivets and around which the elongated bar pivots.

4. The orthopedic hinge assembly according to claim 2 wherein an axial hole in the cam gear accommodates one of the rivets and around which the cam gear pivots.

5. The orthopedic hinge assembly according to claim 1 wherein indicia indicating extension is associated with the first slot and indicia indicating flexion is associated with the second slot.

6. The orthopedic hinge assembly according to claim 1 wherein a stop integral with an end of each adjustment screw engages a cam surface of the cam gear to move the cam gear to a desired position to cause extension or flexion of the second elongated bar with respect to the first elongated bar.

7. A knee splint having an orthopedic hinge assembly mounted on each side of a patient's knee within side pockets of the knee splint, the orthopedic hinge assembly comprising:

(a) a top exterior plate containing indicia on an exterior surface and an opposed bottom exterior plate, a pair of spaced apart slots in the top exterior plate aligned with a corresponding pair of spaced apart slots in the bottom exterior plate, a thumb wheel threaded to a screw, protruding through each pair of slots;

(b) a first elongated bar having a first end portion insertable into a first side pocket on the knee splint and having a second end portion containing spaced apart slots in alignment with the slots on the top and bottom exterior plates accommodating the thumb wheels;

(c) a second elongated bar having a first end portion insertable into a second side pocket on the knee splint and having a second end portion integral with gear teeth;

(d) a cam gear juxtaposed to the second end portion of the first elongated bar engageable with the gear teeth at the second end portion of the second elongated bar;

(e) the second end portion of the first elongated bar, the second end portion of the second elongated bar and the cam gear enclosed by the top and bottom exterior plates; and (f) means for joining the exterior plates together to retain the thumb wheels in position so that turning of the thumb wheels move screws that adjust elongation and flexion of the second elongated bar with respect to the first elongated bar.

8. The orthopedic attached to the knee splint of claim 7, wherein the hinge assembly first elongated bar has a narrow first end portion and a wider second end portion containing the spaced apart slots accommodating the thumb wheel and a second pair of spaced apart slots accommodating the screw on which the thumb wheel turns.

9. The orthopedic hinge assembly according to claim 8 wherein each screw has a stop at one end engaging a surface of the cam gear.

10. The orthopedic hinge assembly according to claim 8 wherein the means for joining the exterior plates together are multiple rivets.

11. The orthopedic hinge assembly according to claim 10 wherein the second end portion of the second elongated bar has a hole through which a rivet traverses and the rivet supports pivoting of the second elongated bar.

12. The orthopedic hinge assembly according to claim 10 wherein the cam gear has a hole through which a rivet is accommodated and around which the cam gear pivots.

13. The orthopedic hinge assembly according to claim 8 where in the hinge assembly components are made from stainless steel.

14. The orthopedic hinge assembly according to claim 8 wherein the hinge assembly components are made from heavy duty aluminum.

15. An orthopedic hinge assembly for use with an orthopedic device comprising:

(a) a top and bottom exterior plate with a first and second spaced apart slot on each top and bottom exterior plate, the first slot on the top exterior plate aligned with a first slot on the bottom exterior plate and the second slot on the top exterior plate aligned with a second slot on the bottom exterior plate;

(b) a first elongated bar having a first end portion attachable to the orthopedic device and having a second end portion containing means to support first and second thumb wheels, each thumb wheel threadably mounted on a screw, the first thumb wheel protruding through the first aligned slots in the top and bottom exterior plates and the second thumb wheel protruding through the second aligned slots in the top and bottom exterior plates;

(c) a second elongated bar having a first end portion adapted to be attached to the orthopedic device and having a second end portion terminated with a circular pattern of gear teeth;

(d) a cam gear juxtaposed to the second end portion of the first elongated bar engageable with the gear teeth of the second elongated bar;

(e) the second end portion of the first elongated bar, the second end portion of the second elongated bar and the cam gear enclosed by the top and bottom exterior plates; and (f) the exterior plates having corresponding aligned holes through which rivets traverse to retain the hinge assembly together.

16. The orthopedic hinge assembly according to claim 15 wherein the second end portion of the second elongated bar has a hole through which a rivet protrudes and on which the second elongated bar pivots.

* * * * *